(12) United States Patent
McKay

(10) Patent No.: US 8,524,265 B2
(45) Date of Patent: Sep. 3, 2013

(54) MEDICAL IMPLANT SHEETS USEFUL FOR TISSUE REGENERATION

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1615 days.

(21) Appl. No.: 11/506,078

(22) Filed: Aug. 17, 2006

(65) Prior Publication Data
US 2008/0044449 A1    Feb. 21, 2008

(51) Int. Cl.
*A61F 2/00*    (2006.01)
*A01N 59/26*    (2006.01)

(52) U.S. Cl.
USPC .......................................... 424/423; 424/602

(58) Field of Classification Search
USPC .................................. 424/423, 602
See application file for complete search history.

(56) References Cited

U.S. PATENT DOCUMENTS

| | | | |
|---|---|---|---|
| 5,108,399 A | 4/1992 | Eitenmuller | |
| 5,162,114 A | 11/1992 | Kuberasampath et al. | |
| 5,201,745 A | 4/1993 | Tayot et al. | |
| 5,206,028 A | 4/1993 | Li | |
| 5,366,507 A | 11/1994 | Sottosanti | |
| 5,626,861 A | 5/1997 | Laurencin et al. | |
| 5,766,618 A | 6/1998 | Laurencin et al. | |
| 5,847,023 A | 12/1998 | Viegas et al. | |
| 5,977,204 A | 11/1999 | Boyan et al. | |
| 6,080,194 A | 6/2000 | Pachence et al. | |
| 6,169,046 B1 | 1/2001 | Shikata et al. | |
| 6,344,496 B1 | 2/2002 | Niederauer et al. | |
| 6,406,498 B1 | 6/2002 | Tormala et al. | |
| 6,417,166 B2 | 7/2002 | Liu | |
| 6,514,286 B1 | 2/2003 | Leatherbury et al. | |
| 6,863,694 B1 | 3/2005 | Boyce et al. | |
| 6,977,231 B1 | 12/2005 | Matsuda | |
| 7,351,280 B2 * | 4/2008 | Khairoun et al. | 106/690 |
| 2005/0010304 A1 | 1/2005 | Jamali | |
| 2005/0085817 A1 | 4/2005 | Ringeisen | |
| 2005/0100578 A1 | 5/2005 | Schmid et al. | |
| 2005/0169893 A1 | 8/2005 | Koblish et al. | |
| 2005/0186240 A1 | 8/2005 | Ringeisen et al. | |
| 2005/0214340 A1 | 9/2005 | Erbe et al. | |
| 2005/0246021 A1 | 11/2005 | Ringeisen et al. | |
| 2005/0283255 A1 | 12/2005 | Geremakis et al. | |
| 2005/0288795 A1 | 12/2005 | Bagga et al. | |
| 2006/0008504 A1 | 1/2006 | Kerr et al. | |
| 2006/0045902 A1 | 3/2006 | Serbousek | |

FOREIGN PATENT DOCUMENTS

| | | |
|---|---|---|
| EP | 0621044 A2 | 10/1994 |
| EP | 0734712 B1 | 10/1996 |
| WO | WO 92/21302 | * 12/1992 |
| WO | 0115711 A1 | 3/2001 |
| WO | 0182989 A1 | 11/2001 |
| WO | 2007069785 A1 | 6/2007 |

OTHER PUBLICATIONS

Liu et al, An Osteoconductive Collagen/Hyaluronate Matrix for Bone Regeneration, Biomaterials 20 (1999) 1097-1108.*
Benque E et al: "Tomodensitometric and histologic evaluation of the combined use of a collagen membrane and a hydroxyapatite space for guided bone regeneration: a clinical report," The International Journal of Oral & Maxillogacial Implants, vol. 14, No. 2, Mar. 1999, pp. 258-264, XP009097616, ISSN: 0882-2786 the whole document.
Database WPI Week 200726, Derwent Publications Ltd., London, GB; AN, 2005-418509, XP002473468 & CN 1 586 416 A (Univ Wuhan Sci & Eng) Mar. 2, 2005 abstract.

* cited by examiner

*Primary Examiner* — Blessing Fubara
*Assistant Examiner* — Jennifer Berrios
(74) *Attorney, Agent, or Firm* — Sorell Lenna & Schmidt LLP

(57) ABSTRACT

Described is a medical device in the form of a thin sheet having granules of a calcium-containing, osteoconductive material interconnected by a thin web of polymeric material. The device includes a first face and a second face, wherein at least the first face is populated with proturbances presenting exposed regions of the calcium-containing, osteoconductive material provided by underlying granules. Methods of making and using such devices are also described, as are methods and devices involving the use of very thin polymeric sheets conformed to bone-ingrowth surfaces of load-bearing orthopedic implants.

36 Claims, 7 Drawing Sheets

MEDICAL IMPLANT SHEETS USEFUL FOR TISSUE REGENERATION

BACKGROUND

The present invention relates generally to sheet form medical implant devices, and in particular aspects to thin implant sheets that can be used for bone graft containment and/or for guided tissue regeneration.

As further background, the regeneration of injured or defective animal or human bone presents unique challenges. For these purposes is it known to implant an amount of additional bone, such as autograft or allograft bone, into a bone defect or other site at which new bone growth is desired. Such bone grafting procedures are among the most common surgical grafting procedures performed today.

As a substitute or addition to actual bone grafts, various bone graft substitutes have been suggested or used to treat defects in the mammalian skeletal system. For example, porous ceramic bone graft substitutes are used to provide a three-dimensional structural framework to conduct bone growth.

Grafting with bone or bone substitutes can present challenges in generating bone in the desired implant region. In many common grafting sites, pressure from the adjacent musculature tends to dislocate or otherwise impede the performance of bone graft material. Efforts have thus been made to prepare actual or substitute bone graft materials that effectively remain at the original implant location and resist the pressures generated by adjacent soft tissues, or to develop barrier devices that minimize or eliminate the affects of the soft tissue on the generation of bone.

Despite efforts in these areas, needs remain for improved or alternative devices and methods for facilitating the generation of tissue at desired sites and especially for regenerating bone at skeletal defect sites. Advantageous such devices would not only assist in retaining the graft material at the implant site, but also have the potential for contributing to tissue development in the grafted region.

SUMMARY

In one aspect, the present invention provides a medical implant device useful for tissue regeneration. The implant device comprises granules of a calcium-containing, osteoconductive material having an average particle diameter greater than about 0.05 mm and less than about 5 mm. A thin web of biodegradable polymeric material interconnects the granules and provides the granules and biodegradable polymeric material as an integral, flexible membrane having a first face and a second face. The membrane has an average thickness no greater than 2 mm. The first face of the flexible membrane has a nonuniform, proturbant surface that is populated with proturbances presenting exposed regions of calcium-containing, osteoconductive material provided by underlying ones of the granules. The exposed regions of calcium-containing, osteoconductive material are separated by regions of the biodegradable polymeric material of the web.

In another aspect, the invention provides a medical implant sheet that includes granules of a calcium-containing, osteoconductive material and a web of biodegradable material interconnecting the granules. The sheet has an average thickness no greater than 2 mm. The medical implant sheet further includes a first face having a surface populated with proturbances defined by surfaces of the granules.

In additional aspects, the invention provides methods for treating patients comprising implanting in the patients medical devices as described herein. In certain embodiments, the medical devices are used in the treatment of comminuted fractures or segmental bone defects, for instance by implanting the devices around the affected bone regions to direct bone growth to repair the fracture or defect.

In another aspect, the invention provides a method for manufacturing a medical device useful for tissue regeneration. The method includes forming a layer of flowable material including a biodegradable polymer. The flowable material has granules dispersed therein, the granules comprising a calcium-containing osteoconductive substance. As incorporated in the liquid layer, the granules have immersed portions immersed in the liquid layer and projecting portions projecting out of the liquid layer. The liquid layer is caused to form a three-dimensionally stable membrane having a web entrapping the granules, the membrane having an average thickness no greater than about 2 mm.

In further aspects, the present invention provides medical implant combinations that include a medical implant device as described herein in combination with a separate bone graft material.

In still further aspects, the present invention provides a medical implant device as described herein in combination with a load-bearing surgical implant. Inventive embodiments include a thin medical implant sheet device having a proturbant surface as described above, wherein the sheet is conformed to a bone-ingrowth surface of a load-bearing orthopedic implant. In such combinations, the sheet desirably has a substantially smooth surface received against the bone-ingrowth implant surface, and an opposite proturbant surface facing away from the bone-ingrowth surface. Further, while osteoconductive granule-containing sheets are advantageous when used in combination with bone-ingrowth surfaces of load-bearing orthopedic implants, similarly-thin polymeric sheets lacking the granules can also be used such combinations, especially wherein the sheets carry an osteogenic substance such as a bone morphogenic protein.

In a further embodiment of the invention, provided is a medical implant device that includes granules of a calcium-containing, osteoconductive material and a reinforcing mesh. A thin web of biodegradable material interconnects the granules and at least partially embeds the reinforcing mesh. The medical implant device includes a first face having a surface populated with proturbances defined by surface contours of the granules.

Additional aspects of the invention, as well as features and advantages thereof, will be apparent from the descriptions herein.

DETAILED DESCRIPTION

Figure 1:
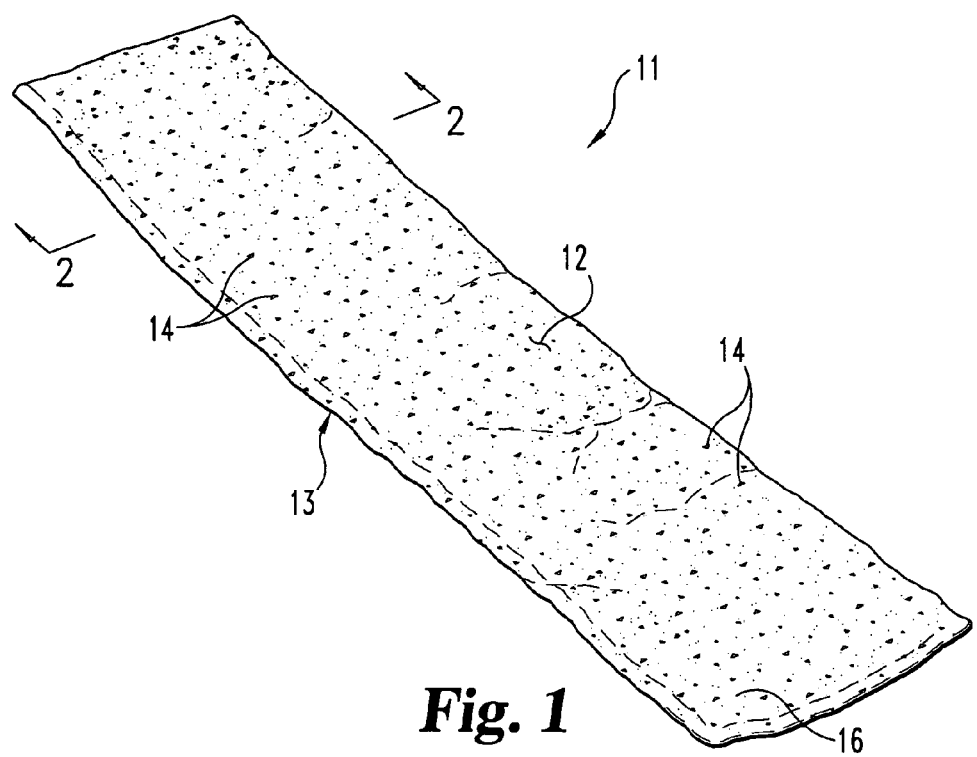
FIG. 1 provides a perspective view of a medical implant sheet in accordance with one embodiment of the invention.

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

As disclosed above, in certain aspects, the present invention relates to medical implants in the form of sheets that are useful in facilitating tissue growth in patients. Advantageous such implant devices include substantially planar sheets including a thin flexible web of biodegradable polymeric material interconnecting osteoconductive granules. The term "granules" as used herein is intended to include particles of material, no matter how prepared. The granules may have regular or irregular shapes, and may for example be individually formed or resultant of crushing of a larger formed body. At least one surface of the flexible membrane is populated with proturbances presenting exposed regions of calcium-containing, osteoconductive material provided by the granules. In particular modes of use, the exposed osteoconductive regions can be positioned to face a target region in which bone growth is desired and can participate in the conduction of bone growth along the surface of the sheet and/or can effectively deliver active agents into the target region or another graft material implanted therein.

A wide variety of osteoconductive materials are known and can be used in the invention. The osteoconductive material can include a natural or synthetic mineral that is effective to provide a scaffold for bone ingrowth. Illustratively, the osteoconductive material may be selected from one or more calcium-containing materials from the group consisting of bone particles, Bioglass®, tricalcium phosphate, biphasic calcium phosphate, hydroxyapatite, calcium sulfate, corraline hydroxyapatite, and biocompatible ceramics. Biphasic calcium phosphate is a particularly desirable synthetic ceramic for use in the invention. Such biphasic calcium phosphate can have a tricalcium phosphate:hydroxyapatite weight ratio of about 50:50 to about 95:5, or about 70:30 to about 95:5, or about 80:20 to about 90:10. In one specific embodiment, said weight ratio is about 85:15. One suitable granular biphasic calcium phosphate is available from Medtronic Sofamor Danek, Memphis, Tenn., USA under the tradename Mastergraft® ceramic granules. This material comprises granules having rounded surface depressions having an average diameter of about 400-600 microns. At the microstructural level, the walls of the surface depressions have micropores with an average size of about 0.6 microns, the granules have a microporosity (size less than 5 microns) of up to about 20%. The Mastergraft® ceramic granules can be crushed and sieved to provide a desired particle size as described herein. Similar synthetic ceramic materials can be prepared using the techniques described in WO2004054633 entitled "Bone Substitute Material" and published Jul. 1, 2004, by extensively fracturing and screening a sintered, macroporous biphasic calcium phosphate block (400-600 micron pores) to provide small granules.

The osteoconductive material can also be or include bone particles, possibly cancellous or demineralized bone particles, but preferably cortical bone particles, ground to provide an average particle diameter among those discussed above for the osteoconductive granular material. Both human and non-human sources of bone are suitable for use in the instant invention, and the bone may be autographic, allographic or xenographic in nature relative to the mammal to receive the implant. Appropriate pre-treatments known in the art may be used to minimize the risks of disease transmission and/or immunogenic reaction when using bone particles as or in the mineral material.

In certain embodiments, xenogenic bone that has been pretreated to reduce or remove its immunogenicity can be used in or as a porous osteoconductive mineral matrix in the implant device. For example, the bone can be calcined or deproteinized to reduce the risks of immunogenic reactions to the implant material.

The osteoconductive material will be in the form of granules having a relatively large size. In embodiments of the invention, osteoconductive granules incorporated into a medical implant device will have an average maximum particle diameter between about 0.05 mm and about 5.0 mm, more typically between about 0.1 and 3.0 mm, and desirably between about 0.1 and 2.0 mm. In certain aspects, the average maximum particle diameter of the granules will be in the range of about 0.2 to about 0.7 mm. Suitable osteoconductive materials can be provided by particulates that are screened to have particles having a distribution of particle diameters. Desirably in such cases, the majority of the particles will have maximum particle diameters within the aforesaid ranges, more desirably with about 80% of the particles within such ranges, and in certain advantageous embodiments with essentially all of the particles having maximum particle diameters within said ranges.

The osteoconductive granules will be included in the device at a substantial level for providing osteoconductive materials for tissue ingrowth. In certain embodiments, the osteoconductive granules will constitute at least about 20% of the weight of the device (dry weight basis), typically in the range of about 15% to about 90% by weight. In more preferred devices the osteoconductive granules will constitute about 20% to about 50% by weight of the device, and certain specific embodiments about 30% by weight.

The granular osteoconductive material can be combined with a biocompatible polymeric material to form a thin membrane. In this regard, a variety of polymeric materials may be used. These include as examples natural polymers such as proteins and polypeptides, including fiber-forming proteins such as collagen and elastin. Synthetic polymers may also be employed, including for example biodegradable synthetic polymers such as polylactic acid, polyglycolide, polylactic polyglycolic acid copolymers ("PLGA"), polycaprolactone ("PCL"), poly(dioxanone), poly(trimethylene carbonate) copolymers, polyglyconate, poly(propylene fumarate), poly(ethylene terephthalate), poly(butylene terephthalate), polyethyleneglycol, polycaprolactone copolymers, polyhydroxybutyrate, polyhydroxyvalerate, tyrosine-derived polycarbonates and any random or (multi-)block copolymers, such as bipolymer, terpolymer, quaterpolymer, etc., that can be polymerized from the monomers related to previously-listed homo- and copolymers. It will be well understood that these and other implantable polymeric materials, or combinations thereof, may be used in aspects of the present invention. Biodegradable natural or synthetic polymers are preferred.

Fibrous materials comprising natural polymers, including fibrous protein materials, can be used in thin sheet devices of the present invention. These include, as examples, fibers comprising collagen, elastin, silk, fibronectin, laminin, or other similar structural, fiber-forming proteins. Insoluble, fibrous demineralized bone matrix (DBM) materials can also be used in the invention, alone or in combination with other fibrous materials disclosed herein.

In some forms, a medical sheet implant of the invention includes a polymeric material containing insoluble collagen fibers, soluble collagen, or both. When used together, the soluble collagen and insoluble collagen fibers can first be prepared separately, and then combined. Both the soluble collagen and the insoluble collagen fibers can be derived from bovine hides, but can also be prepared from other collagen sources (e.g. bovine tendon, porcine tissues, recombinant DNA techniques, fermentation, etc.). Suitable collagen materials for use in the invention can be prepared using these or other techniques known in the literature or can be obtained from commercial sources, including for example from Kensey Nash Corporation (Exton, Pa.) which manufactures soluble collagen known as Semed S, fibrous collagen known as Semed F, and a composite collagen known as P1076. Naturally-derived human collagen or recombinant human collagen can also be used as polymeric materials of devices of the invention.

The polymeric material is used to form a web or membrane interconnecting the granules of osteoconductive material. Any suitable technique for forming such a web may be used. For instance, certain polymeric materials may be converted to a flowable liquid material (including, for example, molten states) or the polymer or a monomeric precursor thereto can otherwise be incorporated within or as a flowable liquid material. Such flowable materials can be provided in a flowable liquid-containing layer in which the granules of osteoconductive material are received. The flowable liquid-containing layer can then be caused to become a non-flowable solid membrane having the granules embedded therein.

In certain modes of preparation, medical sheet implants are prepared by forming a suspension of insoluble polymeric solids and insoluble osteoconductive granules in a liquid, and then removing the liquid in the formation of the sheet. Any suitable liquid can be used for these purposes. The liquid can be an aqueous substance such as water, physiological saline, or phosphate buffered saline. Other liquids can be used alone or in combination with water as well. These may include organic liquids, especially biocompatible organic liquids, for example alcohols such as ethanol.

The concentration of solids in the suspension can be used to help control the ultimate porosity of the polymeric membrane portion of the medical implant device, especially in the case of devices prepared by freeze drying. Generally, higher solids concentrations can be useful in the preparation of less porous membranes and lower solids concentrations can be useful in the preparation of more porous membranes. In certain embodiments herein, the polymeric solids concentration in the suspension will be in the range of about 0.1% to about 10% by weight, and sometimes in the range of about 0.1% to about 5% by weight. It will be understood, however, that other conditions can also be controlled or imparted to vary the porosity of the membrane. For instance, the dispersion pH, lyophilization cycle, and other factors can be varied to vary the porosity of the solid sheet once dried. In addition, the solid sheet can be subjected to further processing to affect its porosity, the further processing including for example re-wetting, compression and crosslinking so as to reduce the porosity and increase the density of the sheet.

A solids dispersion as discussed above can contain the polymeric material in admixture with the granular osteoconductive material, and can be formed into a layer. This can be achieved, for instance, in a mold. In preferred aspects, the granules of the granular material will include portions projecting significantly above the surface of the liquid/polymer mixture. Illustratively, at least some granules from among those in the mixture may have from about 5% to about 95% of their height immersed in the liquid/polymer mixture. It will be understood in this regard that in certain variants of the invention, some granules may also be completely immersed in the liquid/polymer mixture; however, in more desired forms at least a significant percentage of the incorporated granules will include surfaces projecting above the liquid/polymer mixture that will form proturbances exposing osteoconductive regions in the finished sheet device, as discussed herein. The number and percentage of protruding granules can be controlled based upon factors such as the amount and dimensions of the granules relative to the amount and thickness of the liquid/polymer layer, conditions of mixing, and the like.

After forming the granule-dispersed layer, the materials can be dried or otherwise solidified so as to form a solid sheet or membrane having a proturbant surface, wherein the proturbances are caused by the granules. Drying to solidify can be achieved in any suitable fashion, including for example heated drying in an oven or other suitable environment, air drying, or lyophilization. Combinations of these techniques can also be used. The resultant solid material can take on any suitable form and this can be controlled with the shape of the mold or other surfaces against which the starting materials are cast. Simple, substantially planar sheet forms are most desired.

Implant devices of the invention can be crosslinked to improve their strength and integrity. Any suitable technique for crosslinking can be used. These include for example the use of chemical crosslinkers such as gluteraldehyde, formaldehyde, 1,4-butanediol diglycidyl ether, hydroxypyridinium, and hydroxylysylpyridinium. Other crosslinking techniques include irradiation (e.g., E-beam or gamma irradiation), light (e.g., ultraviolet light or other wavelengths of light using an appropriate initiator), or via photooxidation. The device can also be crosslinked under dehydrothermal conditions or acidic conditions. For example, the device can be crosslinked under dehydrothermal conditions by subjecting the composition to a vacuum at elevated temperature. These and other known crosslinking methods will be suitable.

Preferred implant devices of the invention are configured thinly, having a thickness dimension which, on average, does not exceed about 2 mm. As used herein, this expression of thickness pertains to the thickness of the overall device, including both the proturbances and the polymeric membrane structure in between. Average thickness can be routinely calculated as the average of multiple measurements taken at appropriate sample locations on the device. It will be understood that some variation in thickness across regions of the device may be imparted either intentionally or simply as a result of variance due to manufacturing tolerances. Generally speaking, however, planar sheets having a substantially uniform thickness and having an average thickness of less than about 2 mm can be prepared and are preferred. In certain embodiments, the average thickness of devices of the invention will be in the range of about 0.05 to about 2 mm, more desirably in most instances in the range of about 0.1 to about 1.5 mm. In specific advantageous embodiments, a substantially uniform and planar device will be provided having an average thickness in the range of about 0.3 to about 0.8 mm.

As discussed above, the extent to which a surface of the device has granular proturbances can be varied by controlled selection of the dimensions of the granules relative to the thickness of the device. Desirably, the granular material incorporated in the device will include at least some granules that have a maximum diameter that represents at least a substantial percentage of the average thickness of the device. For instance, the granular material can include granules that have a maximum diameter that is at least about 20% and up to about 200% or more of the average thickness of the device, and in certain embodiments at least about 20% up to about 70% of the average thickness of the device. It will be understood in this regard that this does not exclude the possibility of also including smaller granules in the granular material. Such a distribution of sizes can, for example, result in a medical implant device including some partially embedded granules (presenting proturbances of osteoconductive material) and some completely embedded granules. In fact, completely embedded granules residing near the surface of the sheet can also be used to form proturbances on a face of the sheet, and can advantageously increase the surface area of the face in addition to providing exposed osteoconductive calcium-containing material rapidly after implant due to the existence of only a minute thickness of resorbable polymeric material between the granule and the membrane surface. Proturbant-faced devices having some or all of the proturbances provided by such an arrangement are also contemplated as forming a part of the present invention.

In some inventive forms, at least 10% of the granules in the granular material will have a maximum particle diameter that is at least 20% of the average thickness of the sheet, more typically at least 30% of the average thickness of the sheet. In addition, inventive forms are provided in which at least 10% of the granules in the granular material will have a maximum diameter that is at least 100% of, or even greater than, the average thickness of the sheet.

Preferred devices will have at least one surface or face thereof that presents a substantial number of exposed regions of osteoconductive granules, such that a substantial percentage (e.g. at least about 2%) of the area of the surface is occupied by the exposed regions. In certain embodiments, at least one surface of the device can have a surface area constituted at least about 5% of exposed granule portions, or at least about 10% of exposed granule portions. At least some of the exposed granule portions can protrude significantly above adjacent surfaces of the sheet, such as for example at least about 0.05 mm, or at least about 0.1 mm above immediately adjacent surfaces defined by the polymeric material. Protrusions that are greater or smaller than these are also of course possible.

It will be understood that inventive thin sheet devices can also be prepared to have proturbances as described herein on both faces. For instance, to prepare such devices, two thin sheets as discussed above having only one proturbant face can be attached (e.g. crosslinked, bonded, or sutured) back-to-back with the proturbant faces facing outwardly. Alternatively, the polymeric material can be cast or otherwise attached to the granules so that some of the granules partially protrude from each side of the polymeric material. Illustratively, the granules can be layered onto a screen with portions of the granules protruding into openings of the screen, and a viscous polymeric polymeric material can be cast onto such an arrangement so as to leave upwardly extending granular portions extending from the upper surface of the cast layer of polymeric material and downwardly extending granular portions clear of the lower surface of the cast layer of polymeric layer (which does not penetrate or completely penetrate the screen openings to cover the downwardly extending granule portions). The polymeric material can then be hardened as described herein to form the membrane with granular proturbances on each side. Alternatively, a flowable mixture of the polymeric material and granules can be cast and worked onto such a screen, and then hardened, to achieve the dual-sided proturbant membrane. These and other techniques will be suitable for preparing such devices of the invention.

The porosity of medical devices of the invention can be controlled, and in certain embodiments will be selected to provide a relatively dense membrane that is essentially impermeable to the migration of cells through the membrane, but which allows the passage of fluids. Such cell-occlusive membranes can be used to cover or surround and segregate a bone defect from the surrounding soft tissues, and prevent unwanted migration of cells from the soft tissues into the bone defect site during healing. Such cell-occlusive devices can, for example, be used in periodontal and oral applications where the exclusion of rapidly-proliferating epithelial cells is desired. Cell-occlusive devices may also be used to advantage around or otherwise positioned to protect and benefit the healing of long bone fractures.

On the other hand, the porosity of the medical device can be selected to provide a cell-permeable membrane, and/or a plurality of openings or voids can be provided in the device to permit the passage of cells. Thus, in certain embodiments, the membrane itself can be impermeable to cells, but openings can be provided for passage of cells. In other embodiments, the membrane can be permeable to cells, and can include or lack openings for cellular passage. Cell-permeable devices can be used to particular advantage in conjunction with orthopedic implants, for example to allow for the delivery of therapeutic agents such as osteogenic proteins (e.g. BMP) to the bone/implant interface and/or to facilitate bone ingrowth into the implant.

Sheet form devices of the invention can also exhibit desirable physical properties relating to strength and flexibility. In certain embodiments, sheet materials of the invention will possess sufficient suture pull-out strength to be securely sutured in place at an implant site, e.g. exhibiting a suture pull-out strength of at least about 2 Newtons, for example as can be measured by pulling a 5-0 polypropylene suture with a 2 mm bite through the material and measuring the peak force. Additionally or alternatively, sheet devices of the invention can exhibit significant capacity for flexion without fracture or tear, and can for example bent, rolled or conformed to irregular surfaces while maintaining their integrity, especially when manipulated in a wet condition.

Varied aspects of the invention are also provided wherein the implant devices of the invention define a plurality of relatively large openings, for instance having diameters of at least about 1 mm and typically in the range of about 1 mm to 10 mm, more typically about 1 mm to about 5 mm. As discussed above, such openings can facilitate the migration of cells or other tissue related materials through the device to a site at which tissue regeneration is desired. This can be particularly advantageous in situations in which the migration of cells such as mesenchymal cells into a grafted region protected by the inventive implant device is desired. Thus, these perforated devices of the invention provide particular benefit when used as graft containment structures, although other uses are also possible.

Figure 2:
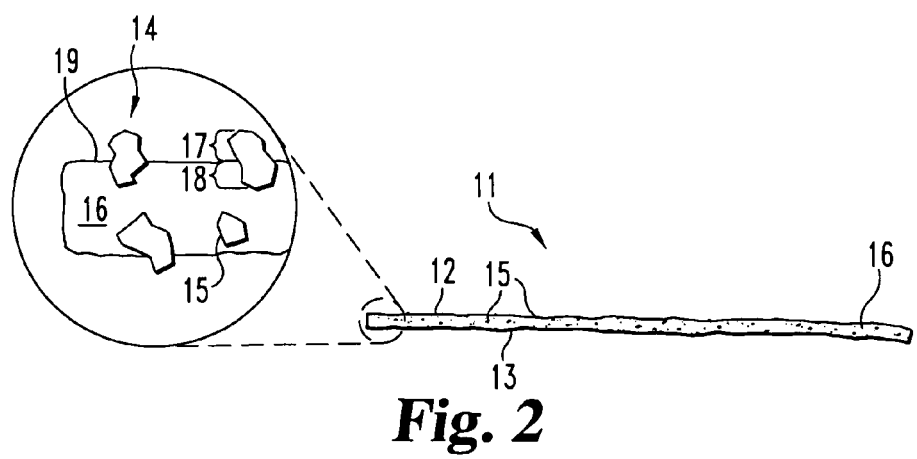
FIG. 2 provides a cross-sectional view of the medical implant sheet depicted in FIG. 1 taken along line 2-2.
Figure 3:
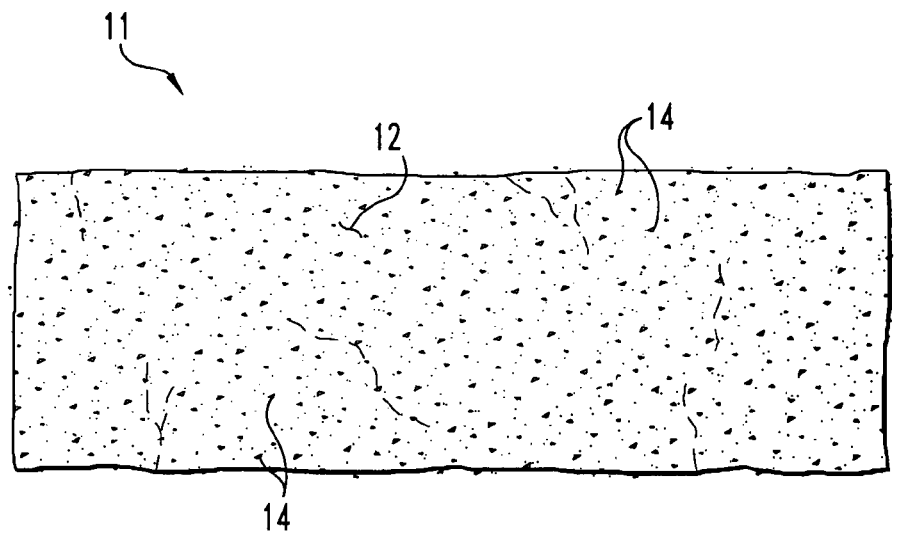
FIG. 3 provides a top view of the medical implant sheet depicted in FIG. 1.

With reference now to FIGS. 1-3, shown in FIG. 1 is a perspective view of an implant sheet 11 of one embodiment of the invention. FIG. 2 provides a cross-sectional view of sheet 11 taken along line 2-2 of FIG. 1. FIG. 3 provides a top view of the implant sheet 11 of FIG. 1. Implant sheet 11 includes a first face 12 and a second face 13. First face 12 is randomly populated with proturbances 14 substantially across the entire surface of face 12. Proturbances 14 are provided by exposed portions of granules 15 that are partially embedded by a web or membrane 16 comprising a polymeric material as described herein. Polymeric membrane material 16 interconnects the granules 15 and forms a unitary implant sheet structure 11. Polymeric membrane material 16 is advantageously a bioresorbable polymeric material, and in certain embodiments comprises a bioresorbable collagenous material.

Granules 15 forming proturbances 14 include a first exposed portion 17 and a second embedded portion 18. Exposed portion 17 is raised above the surface of adjacent regions 19 of the interconnecting polymeric membrane material 16, and presents an exposed and outwardly directed amount of an osteoconductive material. In certain embodiments, second face 13 of sheet device 11 can differ from first face 12 in that second face 13 can be substantially smooth as opposed to having proturbances. A smooth surface of second face 13 can for example be imparted by a surface against which sheet 11 is formed under appropriate conditions therefor, e.g. in a molding or casting process. As will be understood, first face 12 can thus present an increased surface area relative to second face 13, in addition to presenting raised portions of osteoconductive material 17 which can participate in the development of tissues, especially hard tissues such as bone, adjacent to first face 12. However, in other advantageous embodiments, both the first face 12 and second face 13 are proturbant, each presenting exposed granule portions. This can be suitably accomplished by adjusting the properties of the materials of manufacture used, and/or the devices or methods used to prepare the device 11.

Figure 4:
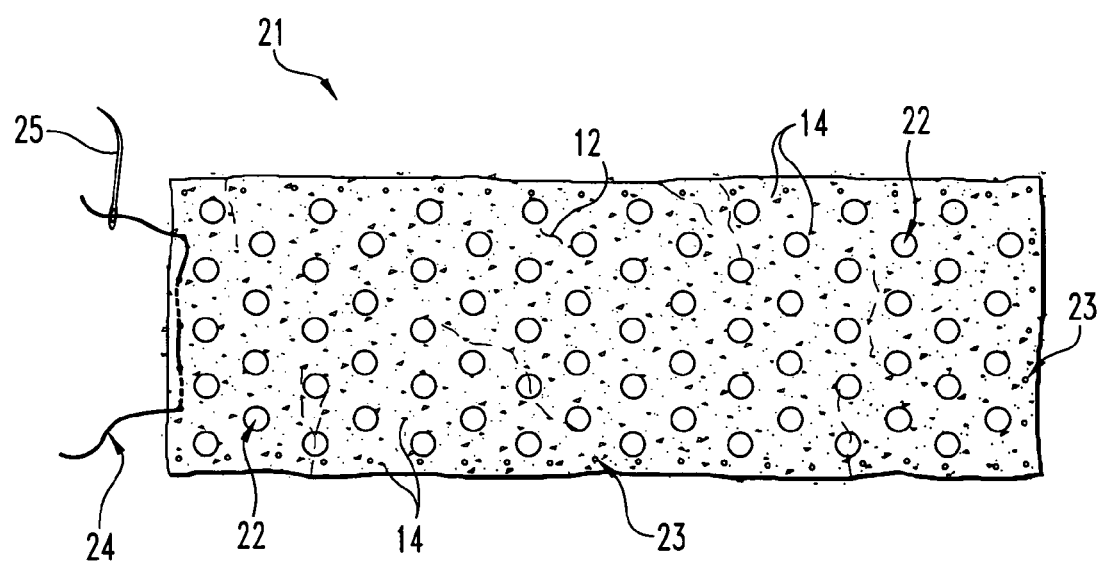
FIG. 4 provides a top view of a medical implant sheet having perforations in accordance with one embodiment of the invention.

With reference now to FIG. 4, shown is another medical implant sheet 21 of the present invention. Implant sheet 21 is similar to that depicted in FIGS. 1-3 and bears corresponding component numbers. However, sheet 21 also includes large openings 22 substantially evenly distributed thereacross, which can serve to allow the passage of cells and other materials through the sheet 21 after implantation. Sheet 21 also includes a plurality of peripheral apertures 23 that are smaller than openings 22, which can for example receive one or more sutures for attaching the device 21 to tissues, to itself, or to another implant component. In this regard, FIG. 4 also depicts a suture 24 woven through several of the peripheral apertures 23, and a surgical needle 25 attached to the suture 24. In certain aspects, suture 24 and/or needle 25 can be provided together with sheet device 21 in a kit format.

Figure 5:
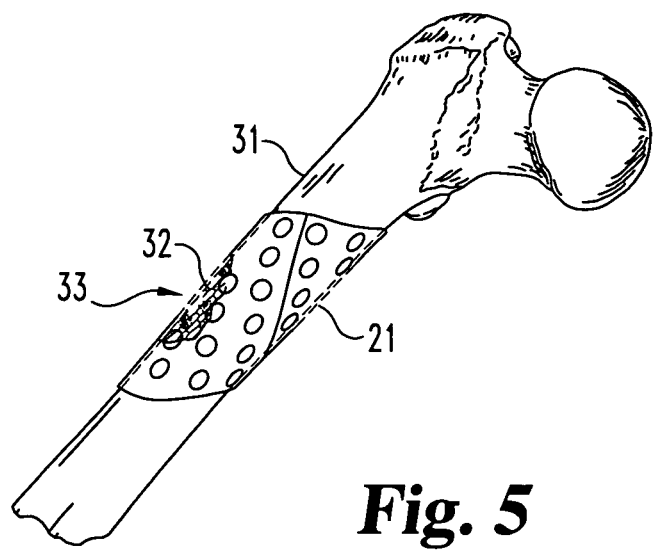
FIG. 5 provides a diagram illustrating the use of the medical implant sheet of FIG. 1 for graft containment.

FIG. 5 illustrates the sheet device 21 of FIG. 4 implanted as a graft containment device at a bone defect in a long bone 31. Thus, sheet 21 is implanted adjacent to and in a fashion which helps to hold the position of a natural or synthetic bone graft material 32 (shown in phantom) inserted in to a defect 33 in bone 31. Defect 33 may, for example, be a defect due to fracture, tissue excision (e.g. in the case of bone cancers), or another cause. Long bone 31 may for example occur in an arm or leg of a human or other patient, for example long bone 31 may be a femur, radius, ulna, tibia or fibula.

Figure 6:
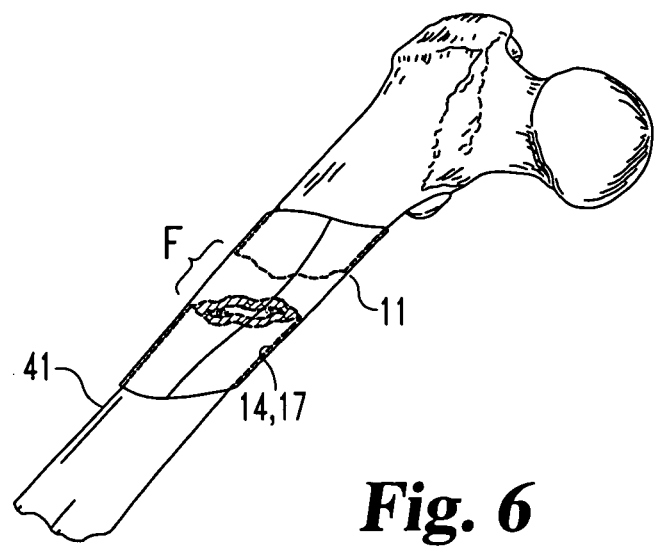
FIG. 6 provides a diagram illustrating the use of a medical implant sheet of the invention for guided tissue regeneration.

With reference to FIG. 6, illustrated is the use of the implant sheet 11 of FIGS. 1-3 for guided tissue regeneration. In particular, sheet 11 is implanted wrapped around a long bone 41 in a region of fracture "F" (see fracture lines shown in phantom). Sheet 11 is positioned so that proturbances 14 and thus exposed osteoconductive material regions 17 are facing inwardly toward the bone, thus immediately providing an osteoconductive surface to facilitate guided tissue regeneration from the adjacent periosteum edges in the healing of long bone 41. Long bone 41 may for example occur in an arm or leg of a human or other patient, for example long bone 41 may be a femur, radius, ulna, tibia or fibula.

Figure 7:
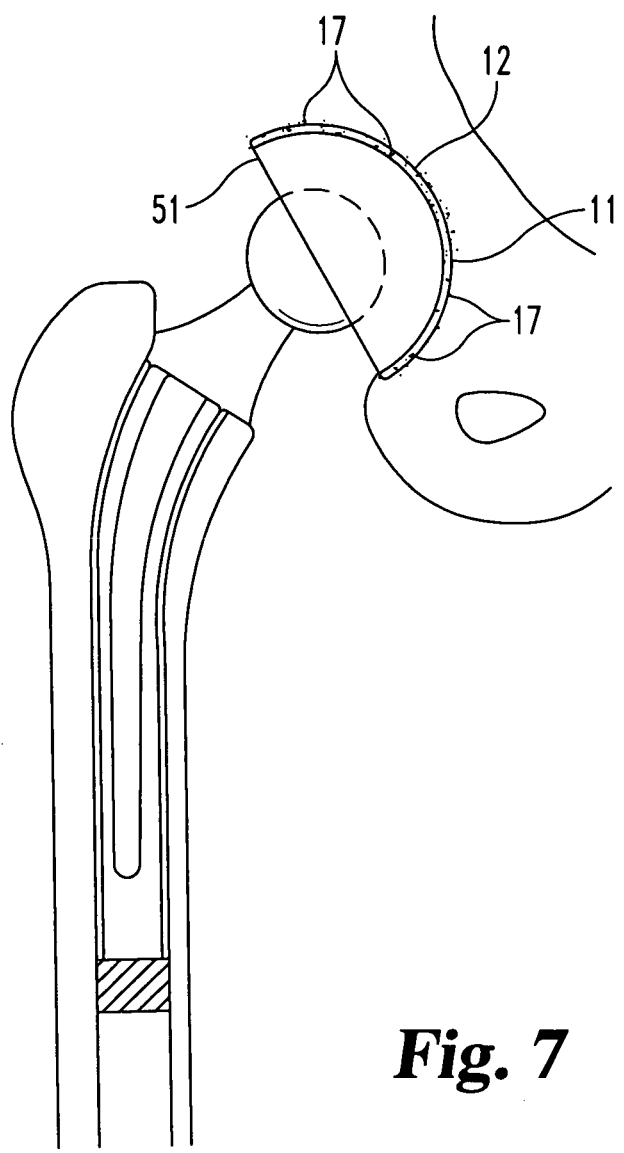
FIG. 7 provides a perspective view of a medical implant sheet of the invention conformed against the rear surface of an acetabular cup surgical implant.

Referring to FIG. 7, shown is sheet implant 11 of FIGS. 1-3 combined with another surgical implant. In particular, an acetabular cup 51, which forms a part of a hip implant, has been combined with sheet implant 11. Sheet implant 11 is implanted in contact with the rear surface of acetabular cup 51 and can help tissue integration into the surface of cup 51, and/or help to fill voids which may occur behind cup 51 when implanted.

Figure 8:
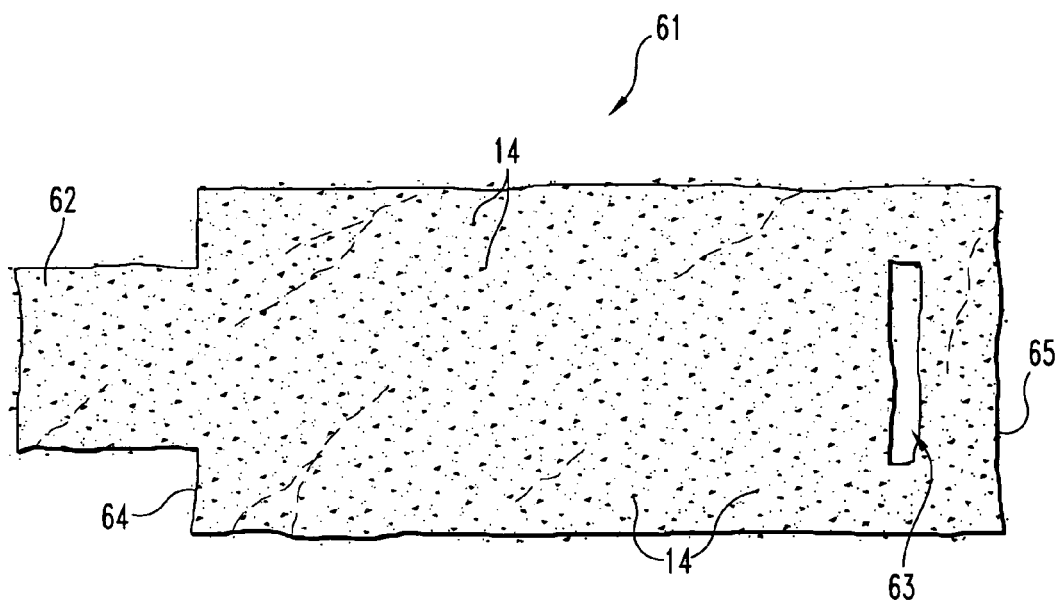
FIG. 8 provides a top view of a medical implant sheet of the invention having a self-contained attachment mechanism.

FIG. 8 provides a top view of a medical implant sheet 61 similar to that shown in FIGS. 1-3, except also including a self-contained attachment mechanism. In particular, sheet 61 includes a tab 62 at one end 64 thereof, and a corresponding slot 63 located proximate to another opposite end 65 thereof. In use, tab 62 can be received through slot 63 to facilitate securing the device to itself, e.g. in a generally tubular configuration such as that which would be used to wrap around a long bone. It will be understood that other mechanisms such as adhesives or sutures could also be used in conjunction with tab 62 and slot 63 to secure the sheet 61 at an appropriate implant location.

Figure 9:
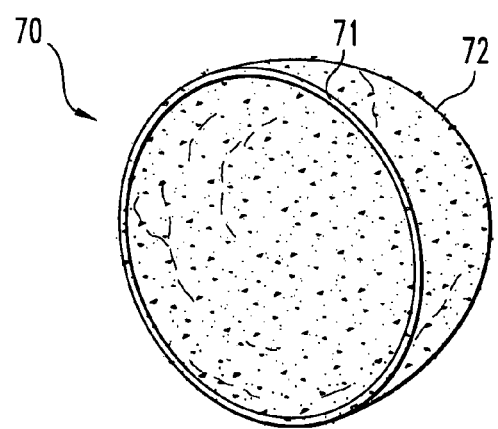
FIG. 9 provides a perspective view of a dome-shaped medical implant sheet of the invention.

FIG. 9 provides a perspective view of a preformed dome-shaped medical sheet implant 70 according to the present invention. Implant 70 includes a rim portion 71 defining a circular or ovate perimeter, and an outer curved surface 72 configured for contact with adjacent bone and/or bone graft material. Dome-shaped implant 70 can, for example, be used to cover the back surface of socket or cup portions of ball-and-socket type implants for hips, shoulders or other joints (see e.g. FIG. 7). Implant 70 can thereby facilitate fixation of the socket portions to adjacent bone via bone ingrowth, either alone or in combination with bone morphogenic proteins or other bioactive substances as disclosed herein. It will be understood that such implants can be any domed shape, including for example generally hemispherical or any other suitable segment of a hollow spherical or other hollow spheroid shape.

Figure 10:
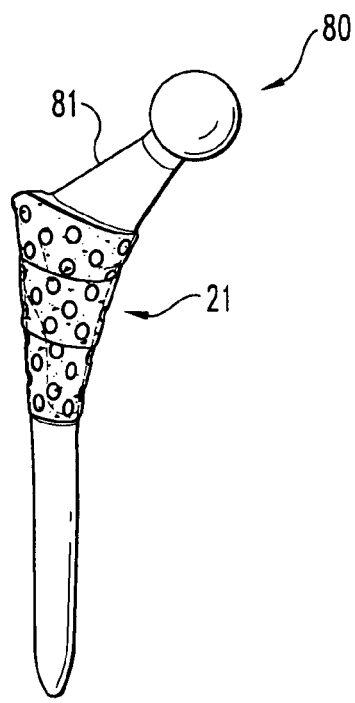
FIG. 10 provides a perspective view of an artificial hip implant component having a bone-ingrowth portion wrapped with a medical sheet implant of the invention.

FIG. 10 provides a perspective view of an implant 80 of the invention including a hip implant component 81 having a stem portion configured for bone ingrowth for fixation, which has been wrapped with a medical sheet implant 21 of the invention. Medical sheet implant 21 can thereby facilitate fixation alone or in combination with bone morphogenic proteins or other bioactive substances as disclosed herein.

Figure 11:
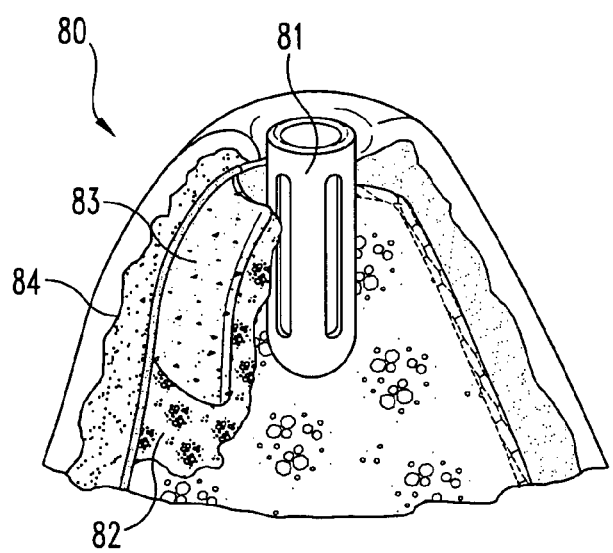
FIG. 11 illustrates a medical sheet implant of the invention in use to retain augmenting bone graft material around a dental implant stem.

With reference to FIG. 11, shown is an implant configuration in which a dental implant stem 81 is received into bone in a patient's jaw. An amount of bone graft material 82 has been implanted to build up bone in the region to provide greater stability to the implant. A medical implant sheet 83 of the invention has been implanted over and around the bone graft material to retain the bone graft material and guide tissue regeneration. Local gingival tissue 84 of the patient has been secured overtop the implant sheet 83.

Figure 12:
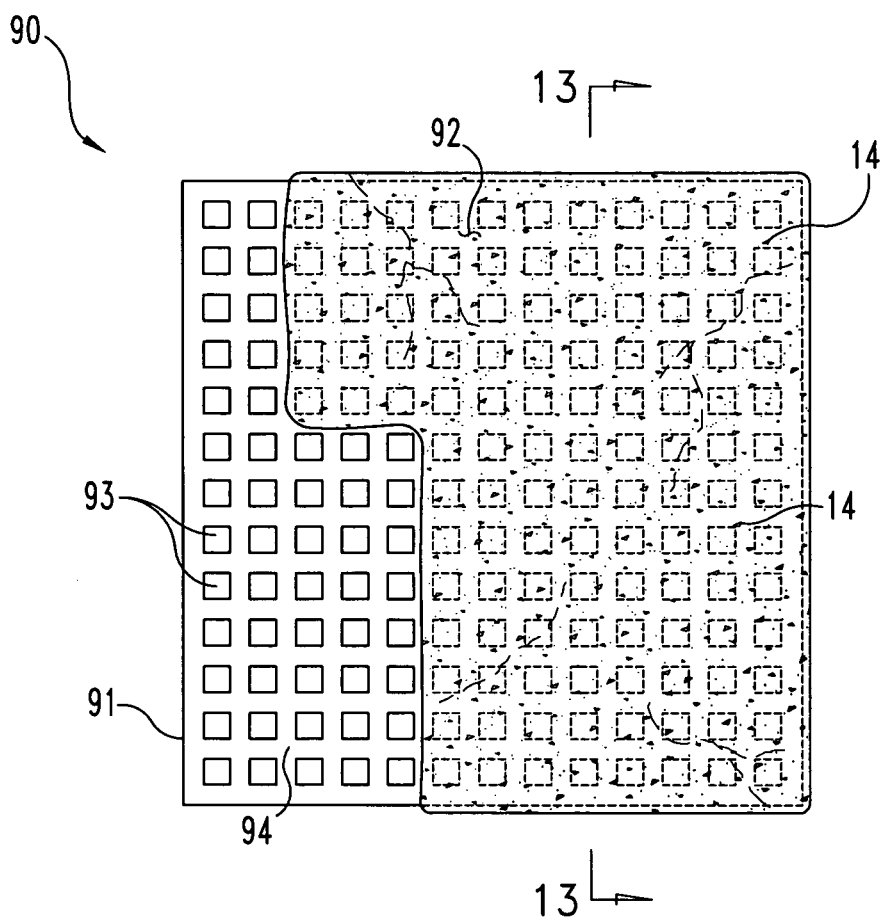
FIG. 12 provides a partial cut-a-way view of a medical sheet implant of the invention reinforced with an internal mesh.
Figure 13:
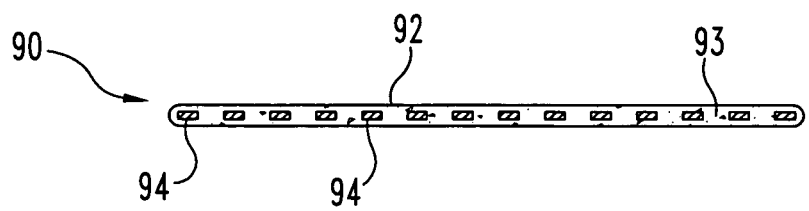
FIG. 13 provides a cross-sectional view taken along line 13-13 of FIG. 12 and viewed in the direction of the arrows.

FIGS. 12 and 13 illustrate an alternative embodiment in which a medical implant sheet includes an internal reinforcement material. FIG. 12 is a partial cut-away view in which the embedding polymeric/granule material has been removed over a portion of medical implant sheet 90 to expose a portion of the embedded reinforcing mesh. FIG. 13 is a cross-sectional view taken along line 13-13 of FIG. 12 and viewed in the direction of the arrows. Thus, the depicted sheet 90 includes a polymeric material 92 incorporating embedded granules 14 at least some of which are surface-exposed as described herein. The sheet 90 further includes a reinforcing mesh 91 that increases the rigidity and/or tensile strength of the sheet. Reinforcing mesh 91 as depicted includes a plurality of openings 93 surrounded by a lattice of struts 94. Mesh 91 can be formed in any suitable manner, including as a integral sheet of material prepared by casting, molding, extruding or other suitable means (potentially post-machined, stamped, etc.) or as a weave or other mesh structure formed with multiple elongate elements such as filaments or wires. Reinforcing mesh 91 can, for example, be formed of a suitable biocompatible plastic or metal material, or both. Reinforcing mesh 91 can be partially or completely embedded within the polymeric material 92, and the sheet 90 can be prepared for example by casting or molding a mixture including the polymeric material 92 and granules 14 around the mesh 91 or against one or both sides of mesh 91. Suitable polymeric materials for the reinforcing mesh 91 include both resorbable and/or non-resorbable polymers. Suitable metals include, for example, stainless steel, titanium or titanium alloys, and superelastic metals such as nickel-titanium alloys (e.g. Nitinol). In certain beneficial embodiments, the mesh is either pre-formed to the shape of a desired implant for bone ingrowth, or is of such a nature as to be conformable to a desired shape at the time of surgery and will retain that shape when implanted. In this manner, the reinforcing mesh 91 can contribute to holding the shape of the overall sheet 90 to guide tissue regeneration to that shape. Illustratively, reinforced sheet 90 can be provided in or deformed to a shape suitable for use in cranial, maxillofacial or dento-alveolar applications in which tissue regeneration is desired. In one application, reinforced sheet 90 can be shaped and used for the augmentation of a human alveolar ridge. In certain embodiments, reinforced sheet 90 can be used in combination with a bone growth inducing substance such as a BMP or other osteogenic protein as described herein, potentially also in combination with other scaffolding or bulking materials such as ceramics, autogenous bone, allogenic bone, collagen, or the like. Reinforced sheets of the invention such as sheet 90 can be relatively thin, for instance having thickness dimensions as disclosed hereinabove, or can be thicker devices, e.g. due to incorporation of the reinforcing mesh.

Implant devices of the invention may be used to carry one or more of a variety of bioactive agents to an implant site. Examples of such bioactive materials include, but are not limited to, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholnergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenlcs, non-steroidal anti-inflammatory agents, steroidal anti-inflammatory agents, antioxidants, vaso-active agents, bone-active agents, osteogenic factors, antiarthritics, and diagnostic agents.

Bioactive agents may also be provided by tissue materials incorporated into, onto or in conjunction with the implant device of the invention. These tissue materials include for instance autologous or allogenic tissue materials, including blood or blood fractions, bone marrow or bone marrow fractions, and/or other sources of cells or other beneficial tissue components derived from the patient to be treated or another suitable animal source.

Bioactive agents such as those described herein can be incorporated homogeneously or regionally into or onto the implant device. Further, they may be incorporated alone or in conjunction with another carrier form or medium such as microspheres or another microparticulate formulation. Suitable techniques for forming microparticles are well known in the art, and can be used to entrain or encapsulate bioactive agents, whereafter the microparticles can be dispersed within the implant device upon its preparation and/or applied to the device after its preparation, e.g. at the time of implant.

In certain embodiments, an implant device of the invention will include one or more substances that induce or generate the formation of bone. Suitable osteogenic materials can include a growth factor that is effective in inducing formation of bone. Desirably, the growth factor will be from a class of proteins known generally as bone morphogenic proteins (BMPs), and can in certain embodiments be recombinant human (rh) BMPs. These BMP proteins, which are known to have osteogenic, chondrogenic and other growth and differentiation activities, include rhBMP-2, rhBMP-3, rhBMP4 (also referred to as rhBMP-2B), rhBMP-5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12, rhGDF-14. For example, BMP-2, BMP-3, BMP-4, BMP-5, BMP-6 and BMP-7, disclosed in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in U.S. Pat. Nos. 5,965,403 and 6,331,612. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of these patents and applications are hereby incorporated herein by reference. Also useful in the present invention are heterodimers of the above and modified proteins or partial deletion products thereof. These proteins can be used individually or in mixtures of two or more. rhBMP-2 is preferred.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-beta superfamily, such as activins, inhibins and TGF-beta 1 (e.g., a heterodimer composed of one monomer each of a BMP and a related member of the TGF-beta superfamily). Examples of such heterodimeric proteins are described for example in Published PCT Patent Application WO 93/09229, the specification of which is hereby incorporated herein by reference. The amount of osteogenic protein useful herein is that amount effective to stimulate increased osteogenic activity of infiltrating progenitor cells, and will depend upon several factors including the size and nature of the defect being treated, and the carrier and particular protein being employed.

Other therapeutic growth factors or substances may also be used in, upon or in conjunction with implant devices of the present invention, especially those that may be used to stimulate bone formation. Such proteins are known and include, for example, platelet-derived growth factors, insulin-like growth factors, cartilage-derived morphogenic proteins, growth differentiation factors such as growth differentiation factor 5 (GDF-5), and transforming growth factors, including TGF-$\alpha$ and TGF-$\beta$.

The osteogenic proteins or other biologically active agents, when used in the present invention, can be provided in liquid formulations, for example buffered aqueous formulations. In certain embodiments, such liquid formulations can be received upon and/or within, or otherwise combined with a sheet form implant device in order to prepare an osteogenic implant. One suitable rhBMP-2 formulation is available from Medtronic Sofamor Danek, Memphis, Tenn., with its INFUSE® Bone Graft product.

Implant devices of the present invention can also comprise progenitor and/or stem cells derived from embryonic or adult tissue sources and/or taken from culture. Illustratively, devices of the invention can be coated and/or infiltrated with cells derived from blood, bone marrow, or other tissue sources from the patient to be treated (autologous cells) or from a suitable allogenic or xenogenic donor source. In certain embodiments of the invention, the devices can be coated or imbibed with an enriched bone marrow fraction, prepared for example as described in US Patent Publication No. 2005/0130301 to McKay et al. published Jun. 16, 2005, publishing U.S. patent application Ser. No. 10/887,275 filed Jul. 8, 2004, which is hereby incorporated herein by reference in its entirety. Thus, the described implant devices can include a bone marrow fraction enriched in connective tissue growth components, that is prepared by centrifuging a biological sample (e.g. from the patient to be treated) to separate the sample into fractions including a fraction rich in connective tissue growth components. The fraction rich in connective tissue growth components can then be isolated from the separated sample, and contacted with the implant device before or after implantation.

In still further embodiments, the present invention provides methods for treating patients that involve implanting in the patients an implant device as described herein. In such uses, the device can be implanted at a site at which tissue growth is desired, e.g. to treat a disease, defect or location of trauma, and/or in some instances to promote artificial arthrodesis. The inventive medical devices can be used as or in surgical implants at, in, on, or near bone defect sites. The flexible and integral character of preferred inventive implants enables their introduction and contouring within voids, defects or other areas in which new tissue growth is desired, and/or in certain embodiments in which the delivery of a bioactive agent is desired.

Illustrative bone repair sites that can be treated with devices of the invention include, for instance, those resulting from injury, defects brought about during the course of surgery, infection, malignancy or developmental malformation. The inventive devices can be used in a wide variety of orthopedic, periodontal, neurosurgical and oral and maxillofacial surgical procedures including, but not limited to: the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired with the implant device include, but are not limited to: the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

In accordance with certain aspects, implant devices of the invention can be used as bone void fillers. In other aspects, the inventive implant devices can be incorporated in, on or around load-bearing orthopedic implants, e.g. implants made of structural materials such as metal or metal alloys such as titanium or cobalt-chromium, or plastics. For instance, the inventive implant devices can be used in primary and revision surgeries involving load-bearing implants to enhance fixation of the load-bearing implants and/or in order to prevent the development of osteolysis in the vicinity of the load-bearing implants. Thus, thin medical implant sheets of the invention can be used in primary and revision surgeries such as shoulder surgeries at the stem of the humeral component; in elbow surgeries, at the stem of the humeral and ulna components; in wrist surgeries, at the stem of the ulna component; in hip surgeries, at the femoral stem, associated with acetabular cup implants, and associated with bone screws; and in knee surgeries, at the femoral stem, at the back side of femoral component articulation, at the tibia stem, the underside of the tibia tray, and at the backside of the patella; and in total shoulder, total hip and total knee replacement surgeries. In this regard, an additional more general aspect of the present invention involves the use of very thin, highly compliant medical sheet devices received against bone-ingrowth surfaces, e.g. porous surfaces designed to receive bone ingrowth for fixation, of these or other load-bearing orthopedic implants. Embodiments are included wherein the sheet device is an inventive device incorporating osteoconductive granules as described hereinabove, or a similar thin, compliant sheet device that lacks the granules. In these embodiments, the thin and compliant nature of the sheets enables their conformance to a wide variety of complex surface geometries, and thus the sheets need not be pre-shaped to fit the bone-ingrowth surface geometry of the load-bearing implant. The thin sheet devices lacking osteoconductive granules, when used in these embodiments, can be prepared using polymeric materials and general methods as described hereinabove, and can have other physical attributes as described hereinabove. When conformed against the bone-ingrowth surface of the load-bearing implant and implanted, the compliant sheet medical implants (lacking or including osteoconductive materials) can promote improved and faster integration of bone into the bone-ingrowth surface thus reducing the chance of loosening, and potentially increasing the longevity of the load-bearing implant. Further, in revision surgery, the conformed medical sheets can facilitate healing of lesions, e.g. behind an acetabular cup. These benefits can be enhanced where the thin implant sheet conformed against the bone-ingrowth surface carries a bioactive material as described herein, especially an osteogenic substance and/or an antibiotic agent. The bioactive agent can be incorporated in the thin implant sheet as manufactured, or can be incorporated at the time of implant by the attending health care provider. In preferred forms, an implant sheet device as described herein is wetted with a liquid pharmaceutical formulation comprising a bioactive agent, for instance a bone morphogenic protein, and then conformed to the bone-ingrowth surface of the load-bearing implant. The combined device can then be surgically implanted in the patient.

The thin implant sheets can be conformed and held against the bone-ingrowth surface of the load-bearing implant using any suitable technique or material. In certain embodiments, an agent is applied to the bone-ingrowth surface, to the sheet, or to both, in order to maintain the position of the sheet conformed against the surface. The holding agent can for example be a biocompatible gel such as a collagen, gelatin, polysaccharide or other gel, or a biocompatible adhesive such as fibrin glue.

Where the conformed sheet incorporates an osteogenic agent, an antibiotic agent, or another bioactive agent as described herein, the sheet can release the agent to the adjacent bone, and/or to an adjacent osteoconductive and/or osteogenic bone graft material also implanted at the defect site. Both natural bone and synthetic bone graft materials as described herein can be used for these purposes. Alternatively or in addition, an osteogenic material can induce bone growth into and through a matrix provided by the thin sheet and enhance bone ingrowth into the bone-ingrowth surface of the load bearing implant.

In other inventive variants, thin implant devices of the invention can be incorporated in, on or around a load-bearing spinal implant device having a compressive strength of at least about 10000 N, such as a fusion cage, dowel, or other device potentially having a pocket, chamber or other cavity for containing an osteoinductive composition, and used in a spinal fusion such as an interbody fusion. One illustrative such use is in conjunction with a load-bearing interbody spinal spacer to achieve interbody fusion. In these applications, the implant device can be placed in and/or around the spacer to facilitate the fusion, potentially delivering an osteogenic agent as discussed hereinabove and/or serving to contain a separate osteogenic graft material in a desired position such as in and/or around the spacer, or within an interbody space.

The present invention also provides medical kits that include at least one medical sheet device as described herein. Such kits can include at least one other medically useful item such as a load-bearing orthopedic implant, and/or a transfer device such as a syringe, and/or a therapeutic substance, for example an osteogenic substance such as a BMP. In one specific form, such a medical kit can include a sheet form implant device of the invention, a BMP in lyophilized form (e.g. rhBMP-2), and an aqueous medium for reconstitution of the BMP to prepare an aqueous formulation that can then be added to the implant sheet to add osteogenic character to the sheet. The sheet can then be implanted and serve to deliver the BMP to a region in which bone growth is desired.

Inventive medical products are also provided that include an implant device as described herein received in sterile condition in medical packaging. Such packaging can for instance include suitable known polymeric films, e.g. in a double pouch or other suitable format. Such products can be terminally sterilized by suitable techniques such as radiation (e.g. e-beam or gamma radiation) or by gaseous sterilants such as ethylene oxide.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are hereby incorporated by reference in their entirety.

The invention claimed is:

1. A medical implant device useful for tissue regeneration, said medical implant device comprising:
   granules of a calcium-containing, osteoconductive material, said granules having an average maximum particle diameter greater than 0.05 mm and less than about 5 mm;
   a thin web of biodegradable polymeric material interconnecting said granules and providing said granules and biodegradable polymeric material as an integral, flexible membrane having a first face and a second face, said membrane having an average thickness of about 0.1 mm to 1.5 mm, the thin web of biodegradable polymeric material being a size to wrap around a bone defect and wrap over itself;
   said first face of said flexible membrane having a nonuniform, proturbant surface protruding greater than 0.1 mm above said thin web of biodegradable polymeric material, said nonuniform, proturbant surface populated with a plurality of the granules oriented such that the plurality of the granules form proturbances presenting exposed regions of calcium-containing, osteoconductive material, said exposed regions of calcium-containing, osteoconductive material separated by regions of said biodegradable polymeric material of said web, and
   said second face of said membrane having a nonuniform, proturbant surface protruding greater than 0.1 mm above said thin web of biodegradable polymeric material, said nonuniform, proturbant surface of said second face being populated with a plurality of the granules oriented such that the plurality of the granules form proturbances presenting exposed regions of calcium-containing, osteoconductive material, said exposed regions of calcium-containing, osteoconductive material separated by regions of said biodegradable polymeric material of said web.

2. The medical implant device of claim 1, wherein:
at least 10% of said granules have a maximum particle diameter of at least 70% of said average thickness of said membrane.

3. The medical implant device of claim 2, wherein:
at least some of said granules have a maximum particle diameter equal to or greater than the average thickness of said membrane.

4. The medical implant device of claim 3, wherein:
at least 80% of said granules have a maximum diameter greater than the thickness of said web.

5. The medical device of claim 1, wherein:
at least 2% of the surface area of the first face of the membrane is occupied by said exposed regions of calcium-containing osteoconductive material.

6. The medical device of claim 1, wherein said membrane defines a plurality of openings.

7. The medical device of claim 6, wherein said openings have a diameter of at least 1 mm.

8. The medical device of claim 1, wherein said biodegradable polymeric material comprises a natural polymer.

9. The medical device of claim 8, wherein said natural polymer is collagen.

10. The medical device of claim 9, wherein said collagen comprises insoluble collagen particles.

11. The medical device of claim 10, wherein said particles are fibers.

12. The medical device of claim 9, wherein said collagen comprises soluble collagen.

13. The medical device of claim 9, wherein said membrane is lyophilized.

14. The medical device of claim 13, wherein said granules have an average maximum particle diameter in the range of about 0.1 to about 2 mm.

15. The medical device of claim 1, wherein said granules comprise calcium phosphate.

16. The medical device of claim 15, wherein said granules comprise biphasic calcium phosphate.

17. The medical device of claim 1, wherein said granules constitute at least 20% by weight of the device on a dry weight basis.

18. The medical device of claim 1, also comprising at least one osteogenic factor.

19. The medical device of claim 18, wherein said osteogenic factor comprises a bone morphogenic protein.

20. The medical device of claim 19, wherein said exposed regions of calcium-containing, osteoconductive material incorporate the bone morphogenic protein.

21. The medical device of claim 20, wherein the bone morphogenic protein is a human protein.

22. The medical device of claim 21, wherein the bone morphogenic protein is selected from BMP-2, BMP-7, and GDF-5.

23. A load-bearing medical device, comprising the medical implant device of claim 1 and a load-bearing orthopedic implant.

24. The load-bearing medical device of claim 23, wherein said medical implant device of claim 1 covers a bone-ingrowth surface of said loadbearing orthopedic implant.

25. The load-bearing medical device of claim 23, wherein said loadbearing implant structure is an interbody spinal spacer.

26. The load-bearing medical device of claim 24, wherein said bone-ingrowth surface is upon an implant stem.

27. The load-bearing medical device of claim 26, wherein said stem is a component of a load-bearing knee implant.

28. The load-bearing medical device of claim 26, wherein said stem is a component of a load-bearing hip implant.

29. The load-bearing medical device of claim 23, wherein said loadbearing orthopedic implant is an acetabular cup, and wherein said medical implant device of claim 1 is received against a back surface of said cup.

30. The medical device of claim 1, also comprising a reinforcing mesh at least partially embedded within said membrane.

31. A method of treating a patient, comprising implanting in the patient a medical implant device according to claim 1.

32. A method for manufacturing the medical device of claim 1 useful for tissue regeneration, the method comprising:
forming a layer of flowable material including a biodegradable polymer, said flowable material having granules dispersed therein, said granules comprising a calcium-containing osteoconductive substance;
said granules having immersed portions immersed in said liquid layer and projecting portions
projecting out of said liquid layer;
causing said liquid layer to form a three-dimensionally stable web entrapping said granules; and
said device having a thickness no greater than about 2 mm.

33. The method of claim 32, wherein said flowable material comprises a natural polymer dispersed in an aqueous medium, and wherein said causing comprises drying.

34. The method of claim 33, wherein said drying comprises lyophilizing.

35. A method for implanting the orthopedic implant of claim 23 in a patient, the method comprising:
providing a load-bearing orthopedic implant of claim 23 having an outer surface for bone ingrowth and attachment;
providing a compliant polymeric sheet having a thickness no greater than 2 mm, the compliant polymeric sheet carrying an osteogenic protein;
conforming the compliant polymeric sheet against said outer surface; and
implanting said load-bearing orthopedic implant in a patient with said compliant polymeric sheet conformed against said outer surface.

36. The method of claim 35, wherein said compliant polymeric sheet comprises a calcium-containing osteoconductive material.

* * * * *